(12) United States Patent
Doubler et al.

(10) Patent No.: US 6,245,112 B1
(45) Date of Patent: Jun. 12, 2001

(54) JOINT PROSTHESIS VARIABLE FLEXIBILITY

(75) Inventors: Robert L. Doubler, Ida, MI (US); John E. Hammill, Sr., Rossford, OH (US)

(73) Assignee: Hammill Manufacturing Co., Toledo, OH (US)

( * ) Notice: Subject to any disclaimer, the term of this patent is extended or adjusted under 35 U.S.C. 154(b) by 0 days.

(21) Appl. No.: 09/515,019

(22) Filed: Feb. 29, 2000

(51) Int. Cl.$^7$ .......................................... A61F 2/32
(52) U.S. Cl. ...................................... 623/22.41; 623/23.45
(58) Field of Search ............................... 623/23.15, 23.45, 623/23.23, 22.46, 22.41, 22.42, 20.15, 18.11; 606/100, 62, 64; D24/155

(56) References Cited

U.S. PATENT DOCUMENTS

| | | |
|---|---|---|
| 2,785,673 | 3/1957 | Anderson . |
| 3,067,740 | 12/1962 | Haboush . |
| 3,820,167 | 6/1974 | Sivash . |
| 3,894,297 | 7/1975 | Mittelmeier et al. . |
| 3,987,499 | 10/1976 | Scharbach et al. . |
| 4,003,095 | 1/1977 | Gristina . |
| 4,004,300 | 1/1977 | English . |
| 4,051,559 | 10/1977 | Pifferi . |
| 4,141,088 | 2/1979 | Treace et al. . |
| 4,167,047 | 9/1979 | Grundei et al. . |
| 4,549,319 | 10/1985 | Meyer . |
| 4,550,448 | 11/1985 | Kenna . |
| 4,750,905 * | 6/1988 | Koeneman et al. ............... 623/22.41 |
| 4,846,839 | 7/1989 | Noiles . |
| 4,851,007 | 7/1989 | Gray . |
| 4,878,917 | 11/1989 | Kranz et al. . |
| 4,919,678 | 4/1990 | Kranz . |
| 4,963,155 | 10/1990 | Lazzeri et al. . |
| 4,995,883 * | 2/1991 | Demane et al. .................. 623/23.23 |
| 4,997,444 | 3/1991 | Farling . |
| 5,002,578 | 3/1991 | Luman . |
| 5,002,581 | 3/1991 | Paxson et al. . |
| 5,062,851 | 11/1991 | Branemark . |
| 5,080,685 | 1/1992 | Boleskey et al. . |
| 5,181,928 | 1/1993 | Bolesky et al. . |
| 5,192,324 | 3/1993 | Kenna . |
| 5,370,706 | 12/1994 | Bolesky et al. . |
| 5,397,360 | 3/1995 | Cohen et al. . |
| 5,441,537 | 8/1995 | Kenna . |
| 5,509,935 | 4/1996 | Fosco et al. . |
| 5,527,316 * | 6/1996 | Stone et al. ........................ 623/23.45 |
| 5,549,702 * | 8/1996 | Ries et al. .......................... 623/23.46 |
| 5,653,765 | 8/1997 | McTighe et al. . |
| 5,702,480 | 12/1997 | Kropf et al. . |
| 5,725,592 | 3/1998 | White et al. . |
| 5,876,459 | 3/1999 | Powell . |
| 5,906,644 | 5/1999 | Powell . |

* cited by examiner

*Primary Examiner*—Pedro Philogene
(74) *Attorney, Agent, or Firm*—McHale & Slavin

(57) ABSTRACT

A joint prosthesis having an intramedullary insert. The intramedullary insert has an elongated body with an attached coil spring. The coil spring may be constructed to provide variable flexibility at different locations along the spring. A control rod is inserted through the coil spring and attached thereto further modifying the flexibility of the coil spring. The shape of the control rod may be varied throughout its length producing different flexibility. The selection of a particular coil spring and a particular control rod resulting in particular joint prosthesis.

19 Claims, 7 Drawing Sheets

JOINT PROSTHESIS VARIABLE FLEXIBILITY

FIELD OF THE INVENTION

The present invention is directed to artificial joints and the structure by which they are secured in the natural bone of the host or patient.

BACKGROUND

The connection by which the artificial joint is held in the host bone is of critical importance to the long term success of any joint replacement surgery. The characteristics of the artificial joint must be matched with the characteristics of the naturally occurring host bone to prevent undue stress resulting in trauma to the natural bone and pain to the host.

Bone prosthesis are either secured in the host with bone cement or without the use of cement. While initially providing a useful connection between the prosthesis and the bone, the earlier cements tended to degrade over time with deleterious results. One approach to overcome this degradation problem was to not use cement at all. This invention relates to installing joint prosthesis without the use of bone cement.

When no cement is used, the connection or fit of the prosthesis within the intramedullary canal of the natural bone becomes more critical. Without the cushioning effect of cement surrounding the intramedullary insert of the prosthesis, there is a requirement for a more accurate matching of the prosthesis insert with the host bone. The prosthesis must, not only, conform to the size of the intramedullary canal of the host bone but to the inherent strength and flexibility or brittleness of the cancellous bone surrounding the intramedullary canal.

These different criteria can create mutually exclusive design requirements, for example, a large insert that must be very flexible because the characteristics of the host bone or a small insert that must be very stiff.

There are various patents and publications directed to the implantation of bone prosthesis without the use of cement each citing the attendant advantages of such procedures. Several patents are directed to the flexibility of joint prosthesis.

U. S. Pat. No. 5,549,702 to Ries et al discloses a one piece or two piece prosthesis in which one end or one portion of the prosthesis is inserted into the intramedullary canal of the host bone. The intramedullary insert of Ries et al has various modifications to achieve a specific flexibility. The insert may be a solid bar or it may be partially tubular. Among the modifications are spiral slots of varying depth. The slots may extend partially through the insert or may extend from a central bore through the entire thickness of the insert forming a coil structure. Other modifications include varying the thickness of the insert along the longitudinal axis. Once each of these variations is manufactured, the flexibility of the insert is permanently set.

U.S. Pat. No. 4,997,444 to Farling discloses a joint prosthesis in which the modulus of elasticity of the intramedullary insert may be varied along the length. The variation results from stacking disks having different characteristics upon a central strut or struts. Farling states that the disks and struts are connected together mechanically or metallurgically bonded together. This indicates that these devices are manufactured with various degrees of stiffness throughout their length and the resulting device cannot or should not be changed thereafter.

U.S. Pat. No. 5,062,851 to Branemark discloses a joint mechanism to be used in smaller bones. The tubular anchoring element has external screw threads for bone contact and a tapering wall thickness. The end portions of the tubular element have longitudinal slits and the wall thickness decreases toward the slit portion. The combination of the slits and thinner walls produce a more flexible end portion of the device.

These references are merely illustrative of the prior art and are not to be considered to be an exhaustive listing.

SUMMARY OF THE INVENTION

The instant invention is a joint prosthesis having an intramedullary insert. The intramedullary insert has an elongated body with an attached or integrated spring like helical construct having a continuous spiraling recess, that is, a coil spring like endpiece. For ease of explanation, the helical construct with recess will be referred to as a coil spring throughout this disclosure. The coil spring provides variable flexibility at different locations along the spring. A control rod is inserted through the coil spring and attached thereto further allows for the flexibility of the coil spring. The shape of the control rod may be varied throughout its length producing different flexibility. The instant invention allows the surgeon to match the stiffness of a particular prosthesis to the strength of the host bone by selecting certain combinations of interchangeable elements of the artificial joint. These elements are then assembled forming an artificial joint having the desired features for use in a particular host. The selection of a particular coil spring and a particular control rod allows joint prosthesis having varying flexibility.

Accordingly, it is an objective of the instant invention to provide a joint prosthesis which can be matched to the natural bone of a particular host.

It is a further objective of the instant invention to provide a joint prosthesis with an intramedullary insert which has a coil structure of particular flexibility. The flexibility results from the properties of the coil, such as the material from which the component is made, the helical slot width, helical slot pitch, cross sectional area of the coil, including outside diameter, inside diameter and width of the coil.

It is yet another objective of the instant invention to provide a control rod inserted through the coil which varies the flex through the shape of the rod. This also allows for differing amounts of flexibility at different points along the length of the intramedullary insert.

It is a still further objective of the invention to provide a plurality of prosthesis elements having differing structural characteristics in a kit. This allows the surgeon to custom build a joint prosthesis to fit the needs of the patient.

While the invention is directed to the major joints of the body, such as the hip, shoulder, elbow and knee, the same principles can be applied to artificial joints between the smaller bones.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

Although the invention will be described in terms of a specific embodiment, it will be readily apparent to those skilled in this art that various modifications, rearrangements and substitutions can be made without departing from the spirit of the invention. The scope of the invention is defined by the claims appended hereto.

Figure 1:
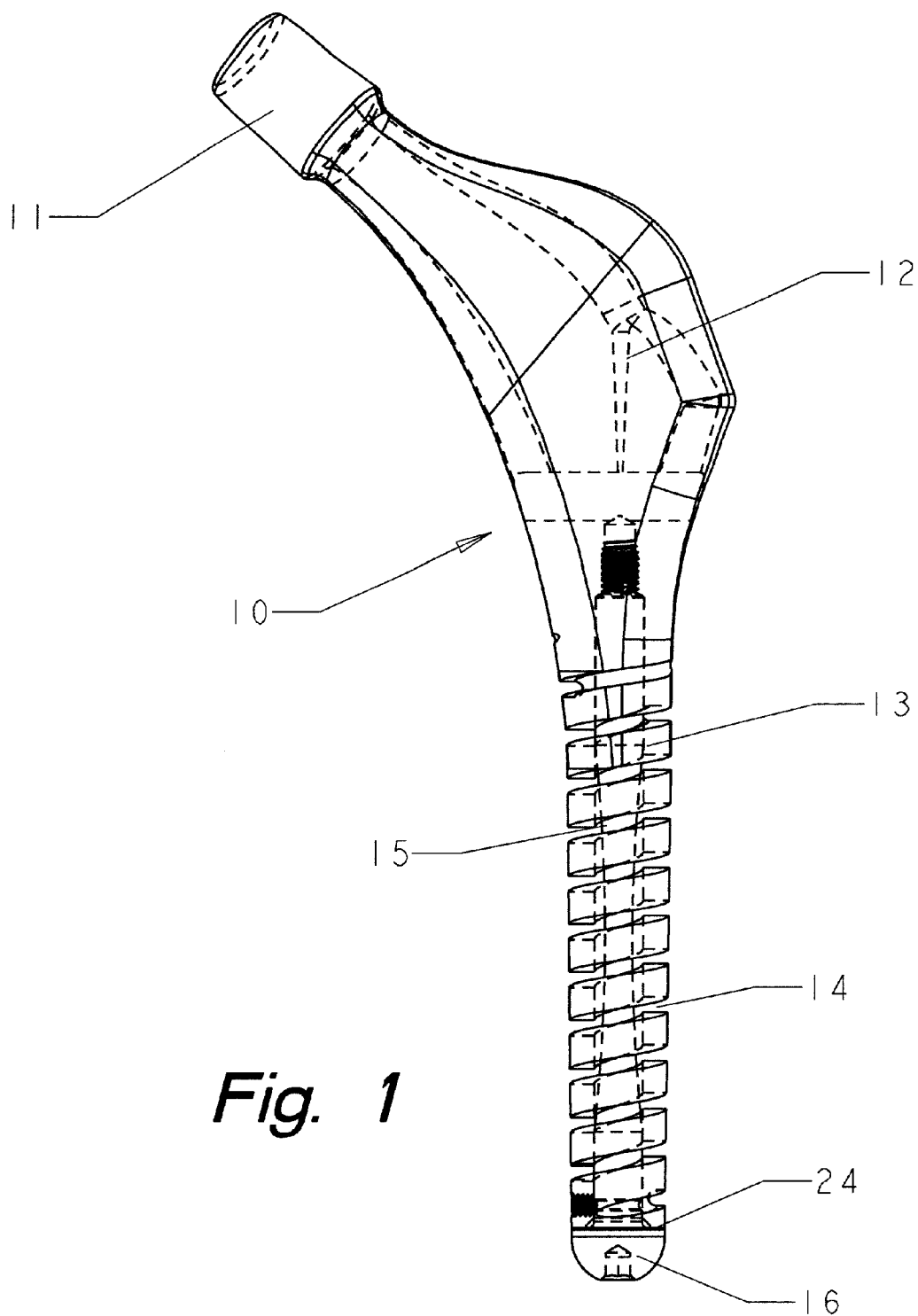
FIG. 1 shows a plan view of a joint prosthesis of this invention.

The joint prosthesis 10 shown in FIG. 1 is directed to an artificial hip replacement. The joint replacement, in this case, a ball joint (not shown) is connected to the fitting 11 which forms one end of the elongated body 12. The elongated body 12 is generally formed in an approximate shape of the particular bone portion that it is replacing, for example either end of the humerus, tibia, fibula, femur, radius, ulna, or smaller bones, to minimize the displacement of the surrounding soft tissues. The lower portion of the elongated body and the coil spring are inserted into the intamedullary canal of the host bone. The prosthesis 10 can be made of most any biocompatible material, including the conventional materials such as titanium, stainless steel, cobalt-chromium steel and composites.

It is most important that the intramedullary insert portion of the prosthesis accommodate, as closely as possible, the size of the intramedullary canal and the strength of the cancellous bone in the shaft of the host bone into which it is inserted. There are many structural variables in the naturally occurring bone, for example, thick or thin areas of the cancellous bone as well as conditions, such as pre-existing traumas or osteoporosis, that require the selection of a particular combination of prosthesis elements.

Figure 6:
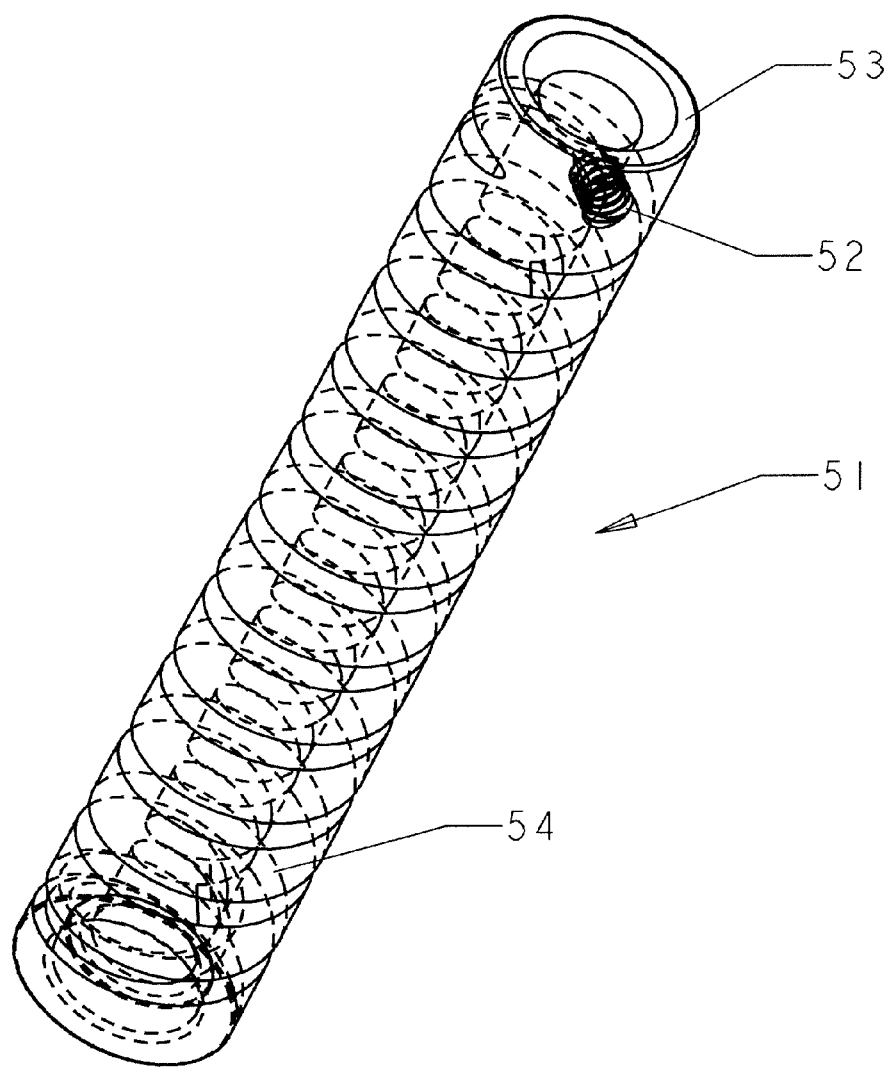
FIG. 6 shows a plan view of another modification of this invention.

The other end of the elongated body 12 is formed in such as manner so as to resemble a coil spring. The flexibility and resiliency of the coil spring is partially determined by the materials from which it is made. The cross sectional area of the coils 13 can be adjusted to modify the flexibility and resilience of the coil spring. The cross sectional area of the coils is determined by the width of the coil 13, the width of the helical slot 14 and the pitch of the helical slot 14. The cross sectional area may also be changed by adjusting the outside diameter and inside diameter of the coil to change the thickness of the coil. The cross sectional area of the coils can be varied along the length of the coil spring to produce different flexibility in different areas, such as shown in FIG. 6. The coil spring could be made in sections (not shown) with differing cross sectional areas and the sections could be assembled end to end to produce a coil spring with different flexibilities along its length.

Control rod 15 is inserted through the coil spring and connected to the other end of the elongated body 12. The control rod 15 provides support and also varies the amount of flexibility along the length of the coil spring. The other end 16 of the control rod is shaped to conform with the other end of the coil spring and forms and end wall. When the control rod 15 is connected to the elongated body 12, the end wall contacts the end of the coil spring and an adjustable amount of compression may be transferred longitudinally to the coil spring. This compression will directly affect the helical slot width.

As shown in FIG. 1, the control rod 15 and the coil spring are secured together to prevent longitudinal separation by a locking ring 24'. The locking ring 24' is in the form of an annular ridge on the interior wall of the coil spring which resiliently fits into an annular depression 24 in the control rod 15. As the control rod 15 is connected to the elongated body, the cooperating surfaces of the locking ring 24' and 24 engage which prevents the control rod and elongated body from becoming disconnected after assembly.

Figure 2:
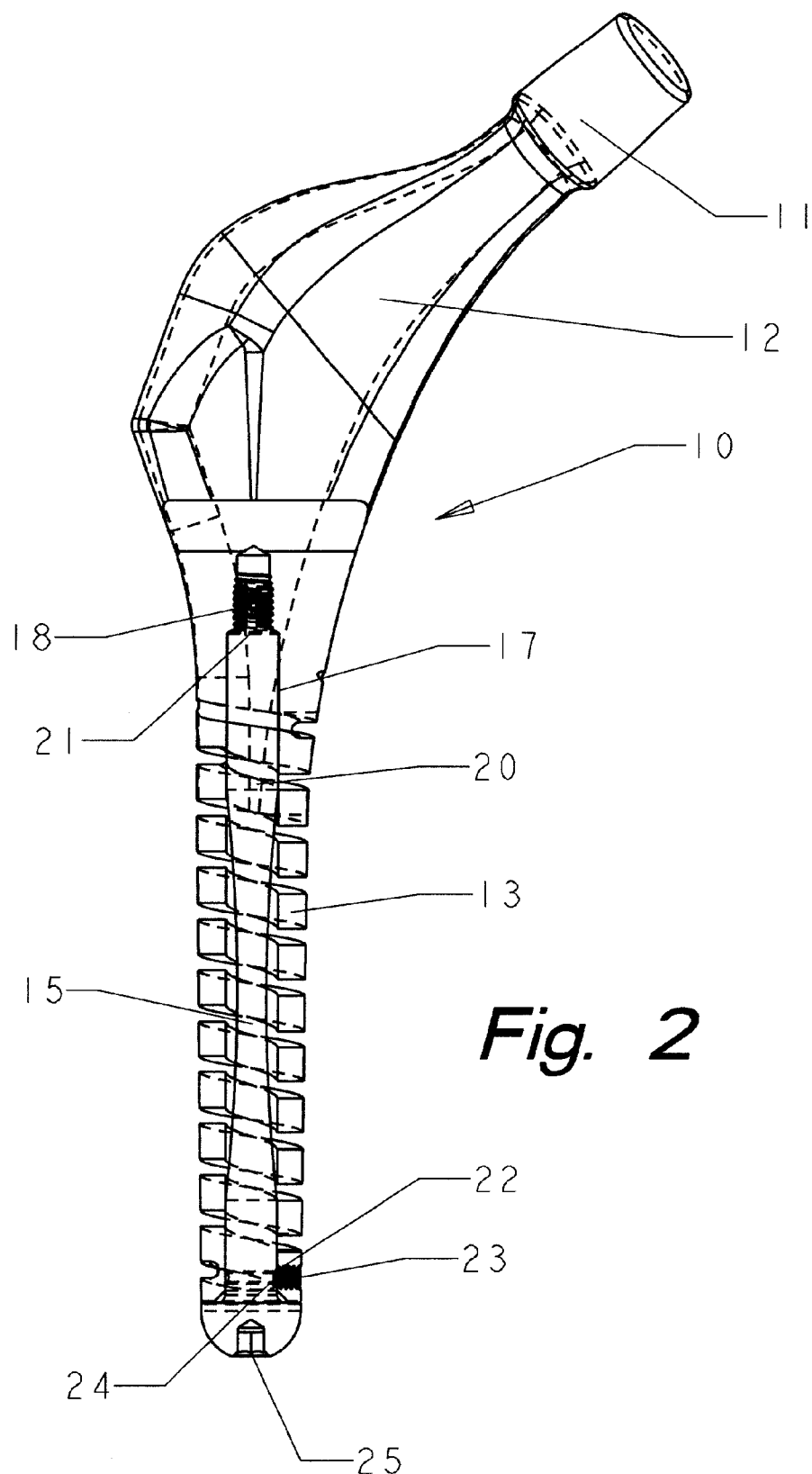
FIG. 2 shows a plan view of a modification of this invention partially in cross section.
Figure 7:
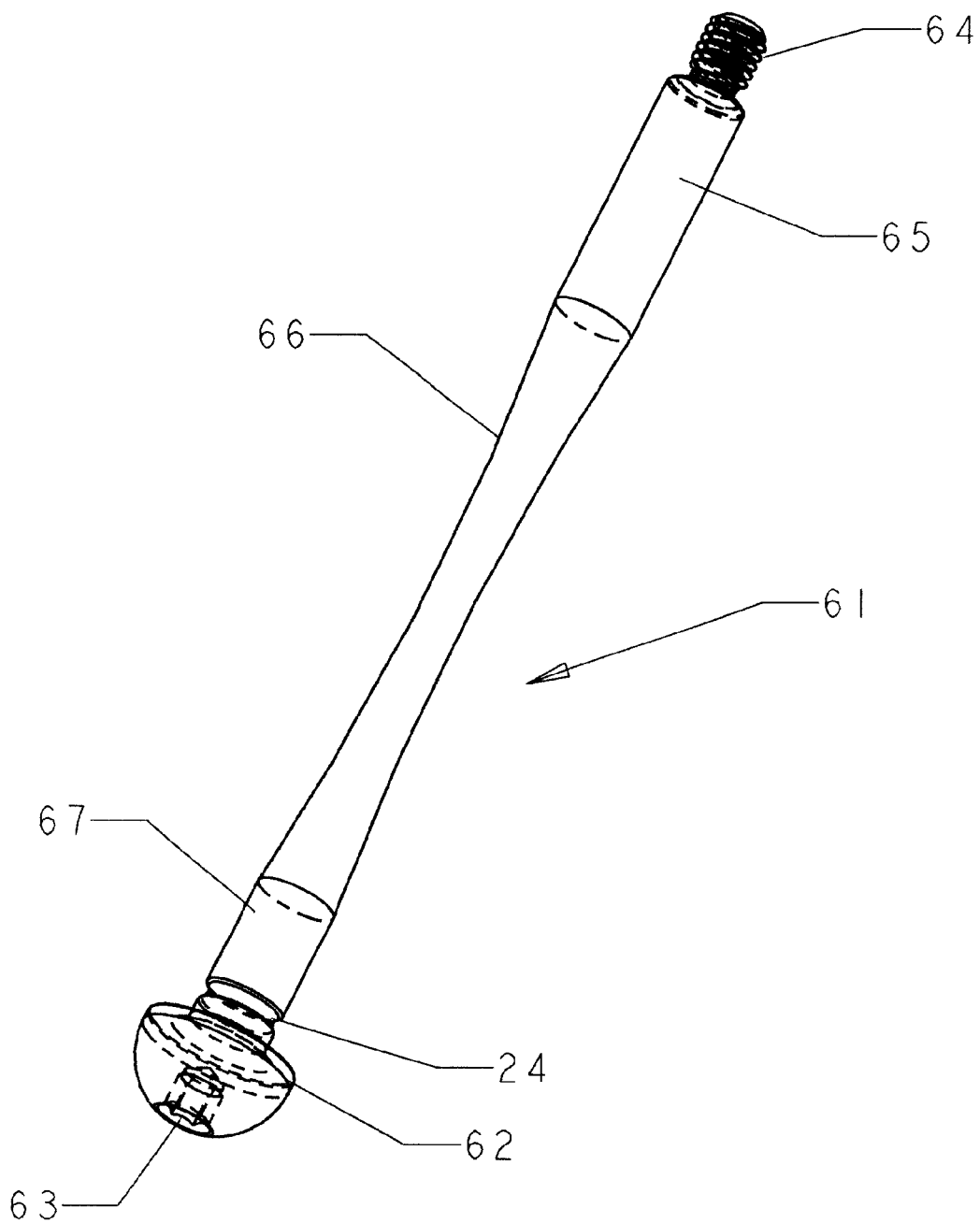
FIG. 7 shows a plan view of a control rod of this invention.

The control rod 15, as shown in FIG. 2 and FIG. 7, may be shaped with different diameters in different longitudinal areas to further modify the flexibility of the intramedullary insert. Such a configuration of the control rod could be in addition to or in lieu of the segmented coil spring construction mentioned above. The particular shape of the control rod used in a particular procedure will be determined by the conditions present along the shaft of the host bone.

In FIG. 2, the other end of the elongated body has a blind bore 19 extending along the axis of the bore of the coil spring. The blind bore 19 has internal screw threads 18 which cooperate with the screw threads 21 on the end of control rod 15. In this modification, the control rod is shown with end portions having a larger diameter than the center portion. In this instance, the blind bore 19 is enlarged at 17 to accommodate the larger diameter portion 20 of the control rod. The blind bore is shown with an internal shoulder engaging the control rod however, the bore could be of uniform diameter and the end of the control rod could contact the end of the blind bore.

The other end of the coil has a fitting for accepting a locking device to hold the coil and the control rod together. A through bore with internal screw threads 22 is shown. When assembled, the inner end of the through bore 22 is located adjacent the annular grove 24 in the control rod 15. A locking screw 23 is threaded through the bore into the annular grove 24 fixing the coil and rod together. Obviously, other conventional locking devices, such as, pins and adhesives could be used.

The other end of the control rod 15 is shown with a fitting 25 to accommodate a tool for assembly of the elements. The particular fitting is not critical but merely has to cooperate with the chosen tools.

Figure 3:
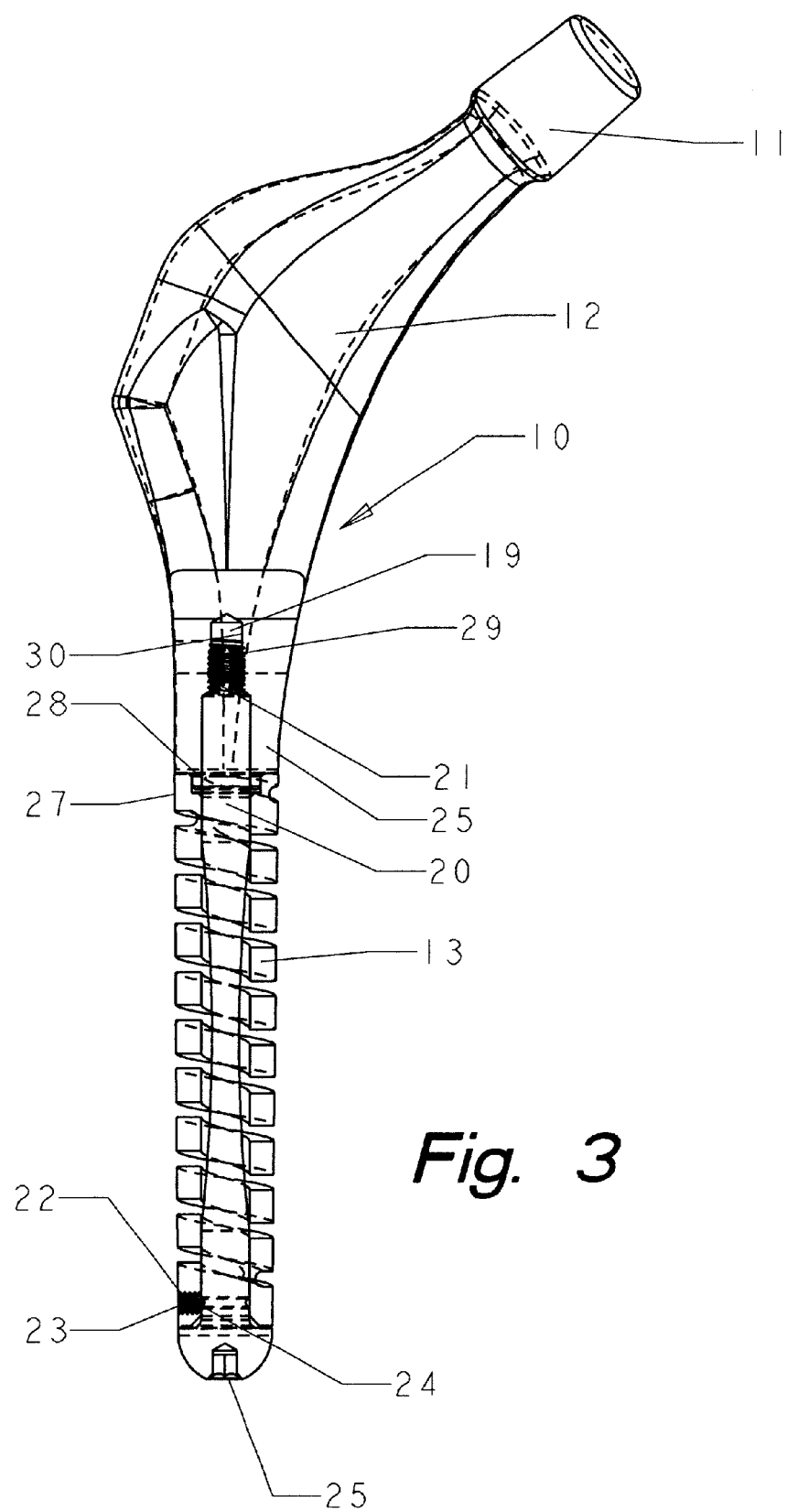
FIG. 3 shows plan view of another modification of this invention partially in cross section.

The length of the elongated body may be adjusted to more closely comply with the host bone. The condition of the host bone may dictate a longer or shorter portion of the host bone be removed and in some instances it may be desired to insert more or less of the elongated body into the intramedullary canal. In FIG. 3 a modified elongated body is illustrated in which the overall length of the elongated may be changed by the use of an insert 26. of course to change the overall length, the elongated body may be used without the insert, as shown in FIG. 2, or it may be used with inserts of different lengths. In FIG. 3, the lower portion of the elongated body has an insert 26 fitted between it and the coil spring. The insert 26 has a through bore to accommodate the passage of the control rod 15. One end of the through bore has internal screw threads 29 which cooperate with screw threads 21 on control rod 15. The end of control rod 15 extends through the insert 26 and engages the internal screw threads 30 in the blind bore 19.

The control rod 15 is shown with a larger diameter portion 20, in FIG. 3, and a reduced diameter end carrying screw threads 21. The transition between these diameters forms a external shoulder on the control rod. The insert 26 is formed with a similar internal shoulder between the large diameter smooth through bore and the smaller diameter screw threaded bore. This modification allows the rotational orientation of the insert to be fixed during assembly. However, the through bore may be of a larger diameter throughout its length.

The other end of the insert 26 has a friction fitting in the form of a tapered annular ring 28. The tapered annular ring 28 fits into a tapered annular cup 27 on the end of the coil spring. The cup 27 and the ring 28 form a friction fit between the insert and the coil spring. Obviously, the friction elements may be reversed.

Figure 4:
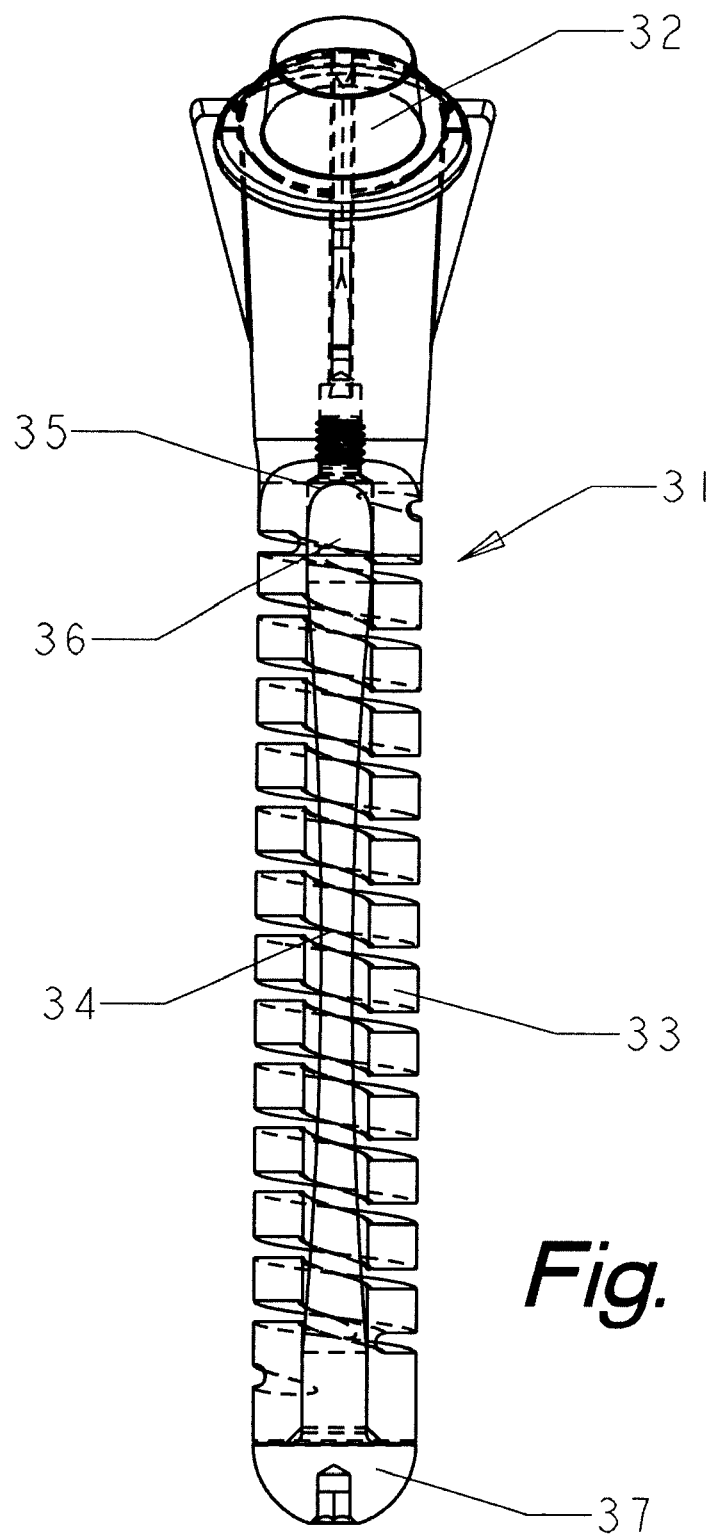
FIG. 4 shows a plan view of another modification of this inanition partially in cross section.

FIG. 4 shows another modification of the prostheses 31. One end of the intramedullary insert carries a friction fitting in the form of a tapered ring 32 for engaging a cooperating fitting on the other end of the elongated body 12 or an insert 26. The control rod 34 has one end 36 which terminates in and conforms to the blind bore 35 formed in the end of the coil spring 33. The other end of the control rod forms the end wall 37 for the coil spring 33.

Figure 5:
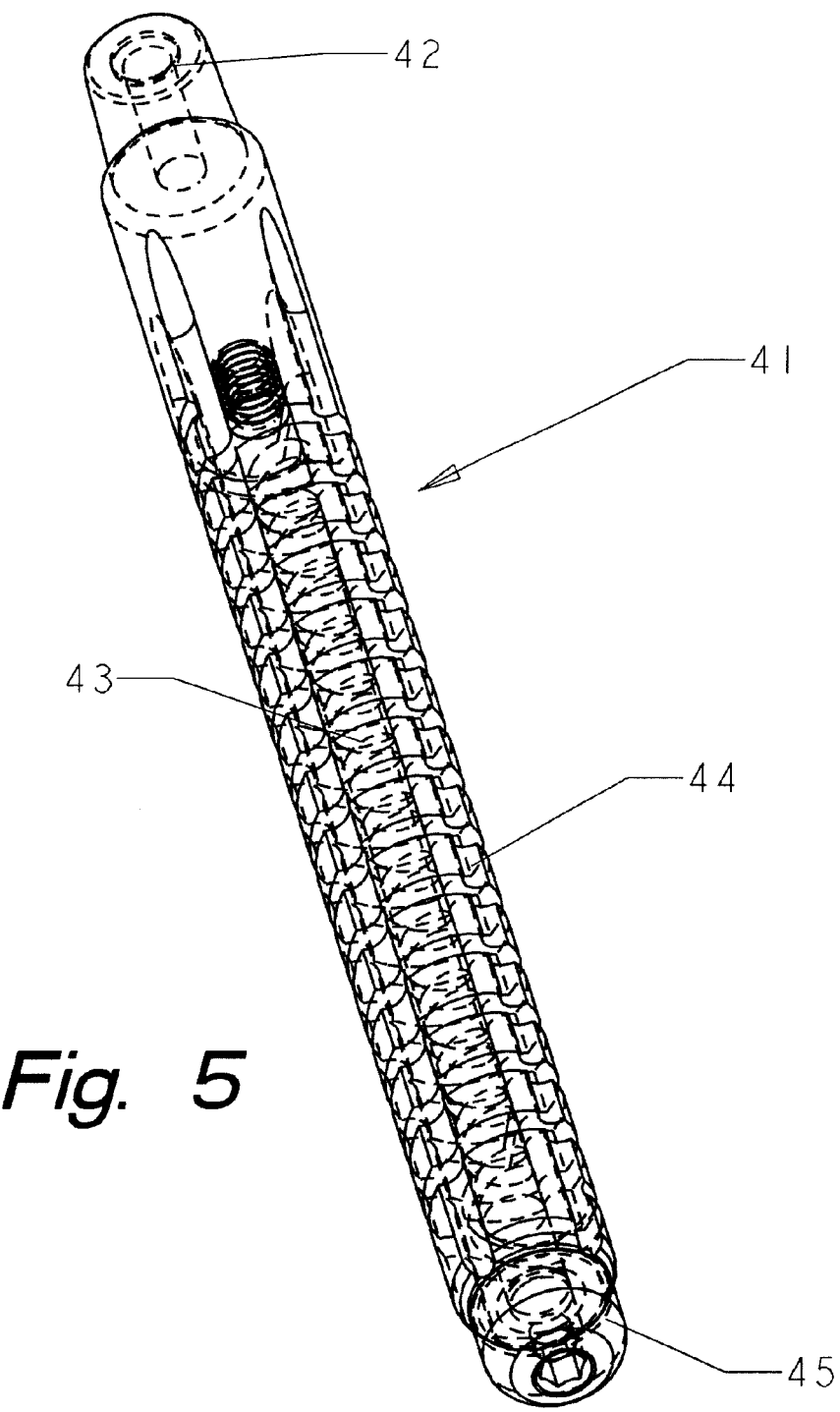
FIG. 5 shows a plan view of another modification of this invention.

FIG. 5 shows another modification of the prosthesis in which the flexibility of the coil spring is varied about its circumference. The intramedullary insert 41 of FIG. 5 has longitudinal grooves formed in the coil spring. These grooves result from different thickness of the coils in certain areas about their circumference. The individual coils of the coil spring have thick portions 43 and thin portions 44. The end of the coil spring is formed with a friction fitting 42 for attachment to the elongated body or to an adapter. The other end of the control rod forms the end wall 45 for the intramedullary insert.

Another modification for changing the flexibility of the intramedullary insert throughout its length is shown in FIG. 6. The coil spring 51 is longitudinally tapered. The coils 54 have decreasing diameter from one end to the other end. The other end has a locking element 52 and a smooth end wall for engaging the control rod 15.

A specific modification of the control rod is shown in FIG. 7. One end of the control rod has screw threads 64 for engaging an elongated body or an insert or both. The other end of the control rod 61 has an end wall 62. The end wall is formed with a fitting 63 therein for use in assembly of the prosthesis. Along the length of the control rod are portions having differing diameters. One end has a larger diameter 65, the other end has a larger diameter which may be the same or different than the diameter 65. The central portion has a smaller diameter 66. The control rod shown in FIG. 7 would clearly be less flexible at the end portions than in the middle. The control rod 61 can also be modified to have the larger diameter in the middle and smaller diameters in the end portions. The use of a tapered control rod is also contemplated wherein the larger diameter may be at either end portion and the smaller diameter at the opposite end.

While the different control rod shapes have been discussed in relation to varying the flexibility of the intramedullary insert, it is clear that structural requirements of the intramedullary canal may dictate a particular control rod.

It is to be understood that while a certain form of the invention has been illustrated, it is not to be limited to the specific form or arrangement of parts herein described and shown. It will be apparent to those skilled in the art that various changes may be made without departing from the scope of the invention and the invention is not to be considered limited to what is described in the specification and drawings.

What is claimed is:

1. A surgical kit for implanting a joint prosthesis in a host wherein the flexibility of the prosthesis is selected as a function of the strength of the host bone comprising:

a) a container holding several interchangeable elements;

b) said interchangeable elements including a plurality of joint replacements, elongated bodies, adapters, intramedullary inserts, control rods, and locking means for securing an intramedullary insert and a control rod after assembly thereof, each of said interchangable elements having differing structural characteristics;

c) said elongated bodies having the general shape of the host bone and having a first end and a second end, said bodies each having a fitting formed integral with said first end for attaching a joint replacement, each said second end containing a fastening means for attaching said intramedullary insert;

d) said intramedullary inserts each formed as a coil spring with one end, another end and a bore; said one end of said coil spring having a cooperating fastening means; said cooperating fastening means constructed and arranged for engagement with the fastening means on said elongated bodies;

e) a plurality of particular sized and shaped control rods having a particular flexibility, each of said control rods having a one end, another end, and a fastening means on said one end;

whereby a particular joint prosthesis having a particular flexibility may be assembled from said kit by selecting a particular shaped elongated body, selecting a particular intramedullary insert with a specific structural characteristic, connecting the fastening and cooperating fastening means, inserting a particular control rod through said bore of said coil spring, said other end of said control rod engaging said other end of said coil spring forming an end wall of said bore, connecting said one end of said rod with said fastening in said elongated body to form a unitary prosthesis.

2. The surgical kit as claimed in claim 1 wherein said fastening means on said elongated body comprises a countersunk hole with internal screw threads and said fastening means on said control rod comprises cooperating external threads.

3. The surgical kit as claimed in claim 1 wherein said other ends of said coil spring and said control rod include cooperating locking elements for preventing longitudinal separation of said control rod and said coil spring whereby a particular locking means is applied to the cooperating locking elements.

4. The surgical kit as claimed in claim 2 wherein an adapter having one end, another end and a longitudinal bore is attached to the second end of said elongated body, said other end of said adapter having a fastening means for engaging said cooperating fastener of said coil spring, said control rod extending through said bore of said adapter and engaging the fastening means in said elongated body.

5. A joint prosthesis for replacing a natural joint occurring between adjacent bones comprising an elongated body of the general shape of the end portion of the natural bone, one end of said elongated body having a fitting adapted to accept a prosthetic element in the shape of a particular natural joint structure, the other end of said elongated body having an intramedullary insert, said intramedullary insert including a particularly sized and shaped coil spring about an open bore, said coil spring having the proximal end connected to said elongated body and a free distal end, the size and shape of said coil spring determining a particular flexibility of said intramedullary insert, and a particularly sized and shaped control rod having a proximal end and a distal end, said control rod inserted through said bore of said intramedullary insert, the size and shape of said control rod determining a particular flexibility of said control rod, said proximal end of said control rod attached to said elongated body, said distal end of said control rod engaging the distal end of said coil spring and forming an end wall of said bore closing said bore, whereby the combination of said size and shape of said coil spring and said size and shape of said control rod cooperate to determine the particular flexibility of said intramedullary insert.

6. A joint prosthesis as claimed in claim 5 wherein said coil spring is comprised of a biocompatible composition formed as a spiral having a continuous helical slot throughout, said particular flexibility resulting from the selection of one or more variables from the group consisting of composition of said spring, helical slot width, helical slot pitch, and cross sectional area of said spiral.

7. A joint prosthesis as claimed in claim 5 wherein said control rod is comprised of a biocompatible composition, said particular flexibility resulting from the selection of one or more variables from the group consisting of composition of said control rod, control rod shape and control rod cross sectional area.

8. A joint prosthesis as claimed in claim 6 wherein said helical slot width varies along said spiral.

9. A joint prosthesis as claimed in claim 6 wherein said helical slot pitch varies along said spiral.

10. A joint prosthesis as claimed in claim 6 wherein said cross sectional area of said spiral varies in one or more of the group consisting of outside diameter, inside diameter, and width of said spiral.

11. A joint prosthesis as claimed in claim 7 wherein said control rod cross sectional area tapers along the length of said control rod.

12. A joint prosthesis as claimed in claim 7 wherein said control rod shape may be any one of the group consisting of uniform diameter, larger diameter in a middle portion and smaller diameter at the end portions thereof, larger diameter at end portions and smaller diameter in the a middle portion thereof, or larger diameter at one end and smaller diameter at an other end.

13. A joint prosthesis as claimed in claim 5 wherein said intramedullary insert and said elongated body are formed separately, said proximal end of said coil spring terminates in an annular friction fitting having a bore communicating with said bore of said coil spring, said second end of said elongated body terminates in an annular mating friction fitting, said annular friction fitting and annular mating friction fittings joined together forming a friction fit, said control rod inserted through said coil spring bore and said friction fitting bore and attached to said elongated body.

14. A joint prosthesis as claimed in claim 13 wherein said proximal end of said control rod is secured within said annular friction fitting of said coil spring.

15. A joint prosthesis as claimed in claim 13 wherein said second end of said elongated body includes an attachment and an adapter, said adapter having a proximal end, a distal end and a bore therethrough, said proximal end of said adapter connected to said second end of said elongated body with said bore surrounding said attachment, said distal end of said adapter having an annular mating friction fitting forming a friction fit with said annular friction fitting on said coil spring, said control rod inserted through said coil spring bore, said adapter bore and attached to said attachment.

16. A joint prosthesis as claimed in claim 15 wherein said attachment comprises a countersunk hole with internal screw threads, said bore of said adapter includes internal screw threads and said proximal end of said control rod carries mating external screw threads.

17. A joint prosthesis as claimed in claim 16 wherein said distal end of said coil spring and said distal end of said control rod have cooperating locking means for preventing separation of said control rod and said coil spring.

18. A joint prosthesis as claimed in claim 13 wherein said distal end of said control rod and said distal end of said coil spring have cooperating locking means for preventing the separation of said coil spring and said control rod.

19. A joint prosthesis as claimed in claim 14 wherein said distal end of said control rod and said distal end of said coil spring have cooperating locking means for preventing the separation of said coil spring and said control rod.

\* \* \* \* \*